United States Patent
Roth et al.

(10) Patent No.: US 8,617,468 B2
(45) Date of Patent: Dec. 31, 2013

(54) PLATELET AGGREGATION TEST AND DEVICE

(75) Inventors: Andrew Roth, Havertown, PA (US); Nicholas J. Veriabo, Springfield, PA (US)

(73) Assignee: Chrono-Log Corporation, Havertown, PA (US)

( * ) Notice: Subject to any disclaimer, the term of this patent is extended or adjusted under 35 U.S.C. 154(b) by 183 days.

(21) Appl. No.: 13/275,402

(22) Filed: Oct. 18, 2011

(65) Prior Publication Data
US 2013/0094998 A1    Apr. 18, 2013

(51) Int. Cl.
| | | |
|---|---|---|
| *G01N 33/00* | (2006.01) | |
| *G01N 27/00* | (2006.01) | |
| *G01N 37/00* | (2006.01) | |
| *B01J 19/00* | (2006.01) | |
| *A61B 5/00* | (2006.01) | |

(52) U.S. Cl.
USPC ...... 422/73; 422/68.1; 422/82.01; 422/82.02; 422/82.03; 422/224; 422/500; 422/554; 436/8; 436/10; 436/63; 436/69; 436/149; 436/150; 436/151; 73/64.41; 600/369

(58) Field of Classification Search
USPC ......... 422/68.1, 73, 82.01, 82.02, 82.03, 224, 422/500, 554; 436/8, 10, 63, 69, 149, 150, 436/151; 73/64.41; 600/369
See application file for complete search history.

(56) References Cited

U.S. PATENT DOCUMENTS

| | | | |
|---|---|---|---|
| 2,555,937 | A | 6/1951 | Rosenthal et al. |
| 4,123,701 | A | 10/1978 | Josefsen et al. |
| 4,301,414 | A | 11/1981 | Hill et al. |
| 4,319,194 | A | 3/1982 | Cardinal et al. |
| 4,591,793 | A | 5/1986 | Freilich |
| 4,822,568 | A | 4/1989 | Tomita |
| 5,601,995 | A | 2/1997 | Exner |
| 6,004,818 | A * | 12/1999 | Freilich et al. ............. 436/69 |
| 7,901,629 | B2 * | 3/2011 | Calatzis et al. ............. 422/73 |

FOREIGN PATENT DOCUMENTS

EP    2182345 A1    5/2010

OTHER PUBLICATIONS

European Search Report dated Jan. 29, 2013.
Calatzis et al., "Multiplate platelet function analysis—application and interpretation".
Goldenberg et al., "A Micromethod to Measure Platelet Aggregation and ATP Release by Impedance", Thrombosis Research, vol. 103, pp. 57-61 (2001).
Toth et al., "Multiple electrode aggregometry: A new device to measure platelet aggregation in whole blood", Thromb. Haemost., vol. 96, pp. 781-788 (2006).

* cited by examiner

*Primary Examiner* — Dean Kwak
(74) *Attorney, Agent, or Firm* — Caesar, Rivise, Bernstein, Cohen & Pokotilow, Ltd.

(57) ABSTRACT

An assembly for testing platelet aggregation including an electrode subassembly that is mounted in a cuvette subassembly for use with relatively small samples containing platelets.

5 Claims, 7 Drawing Sheets

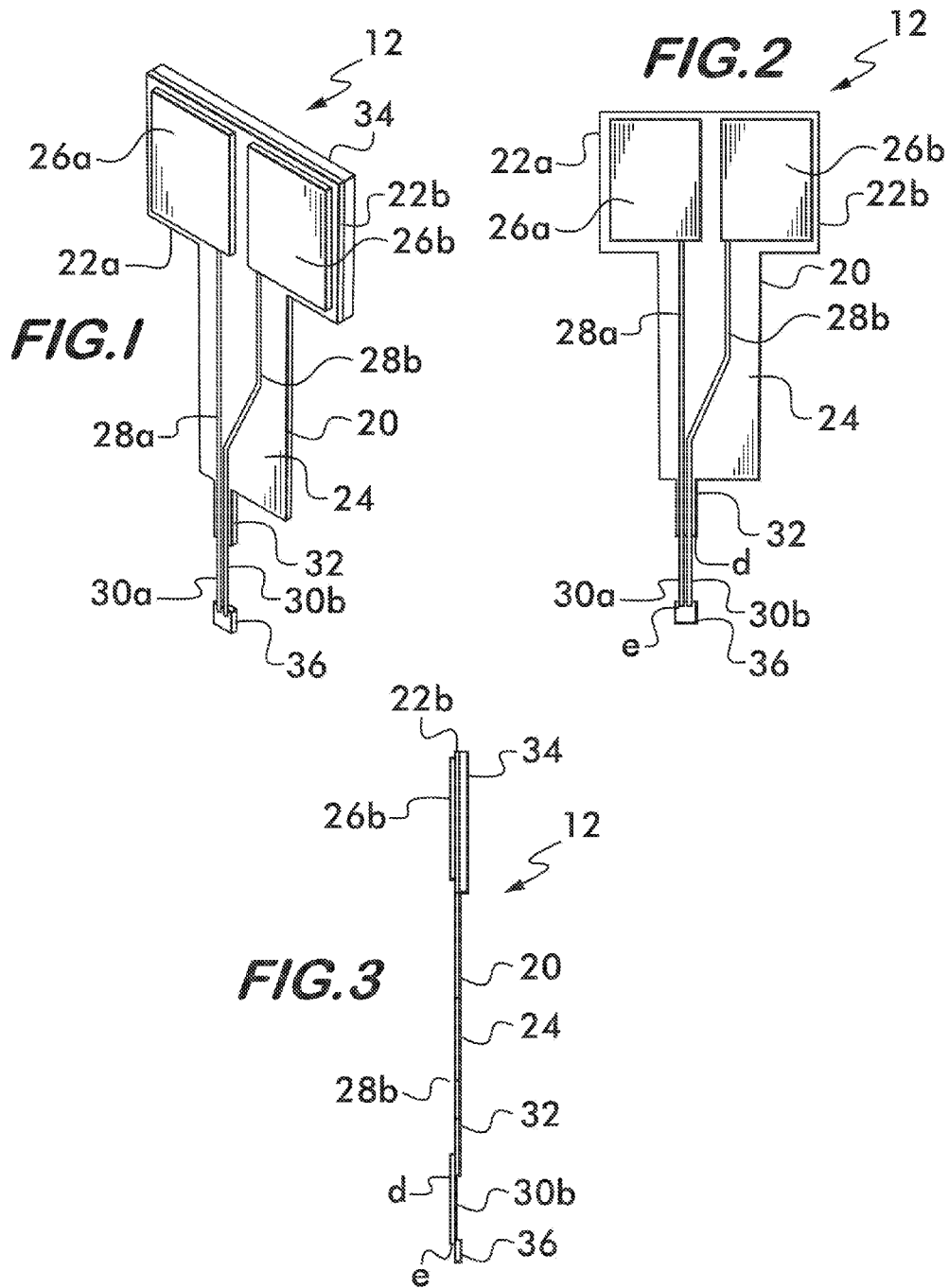

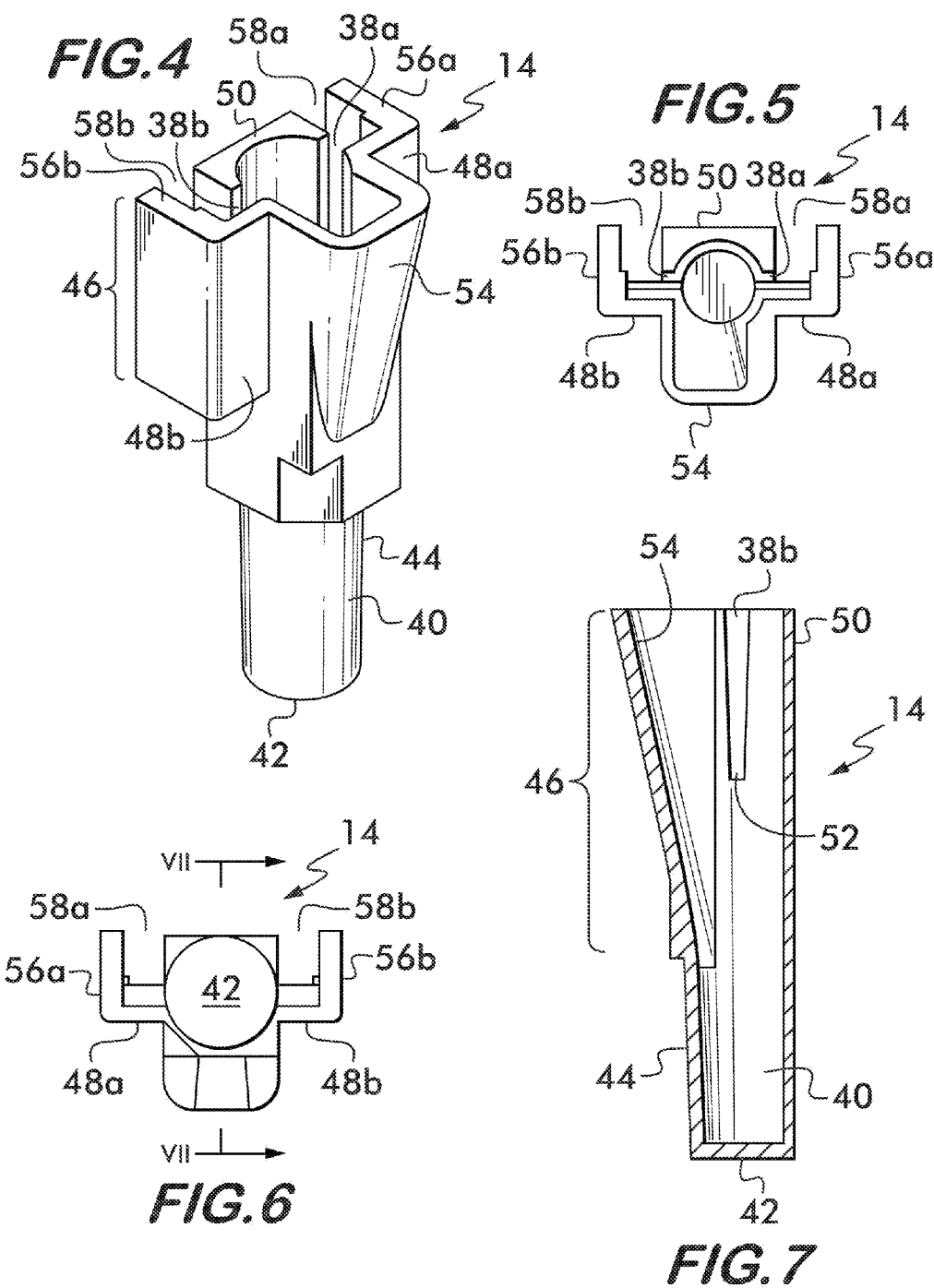

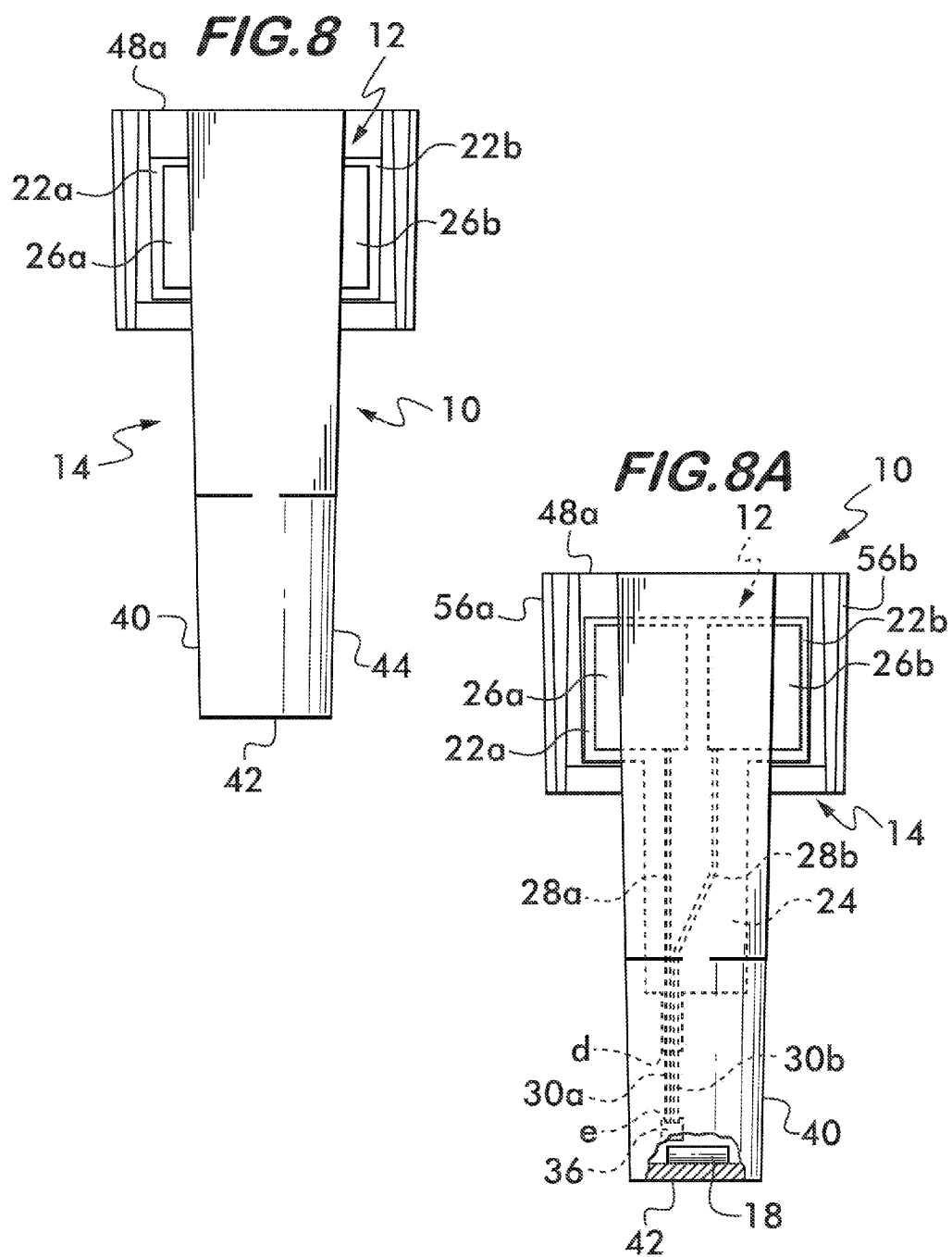

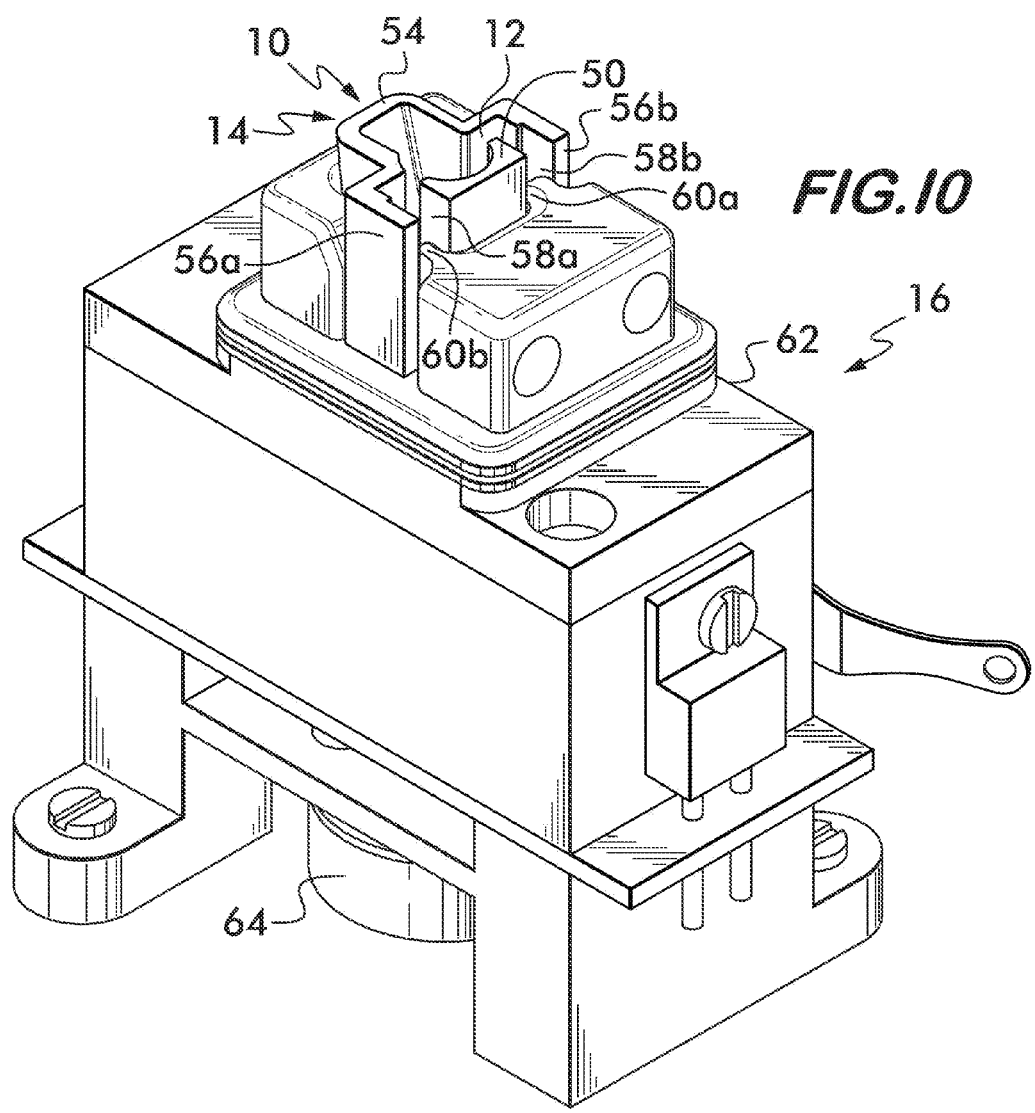

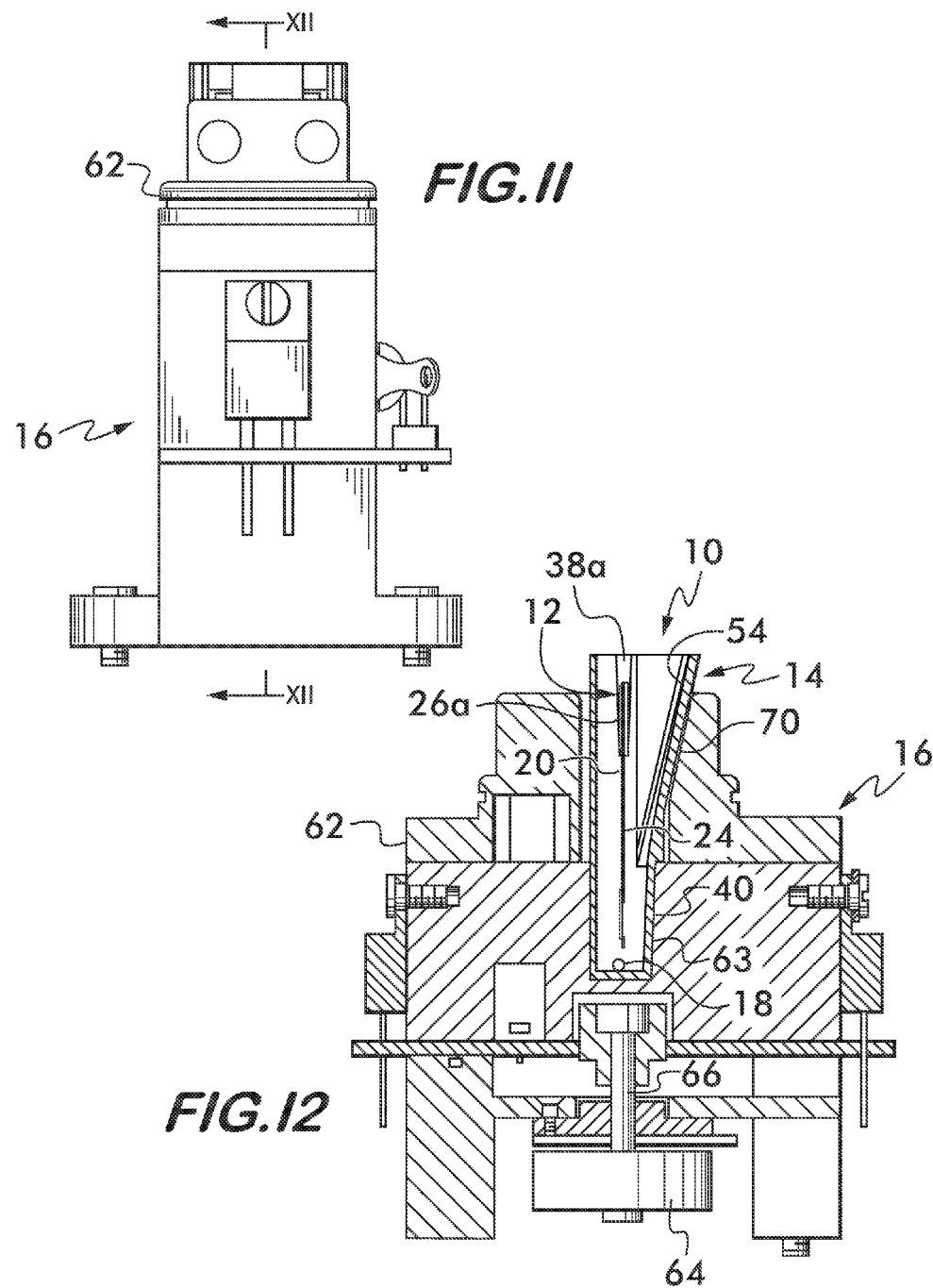

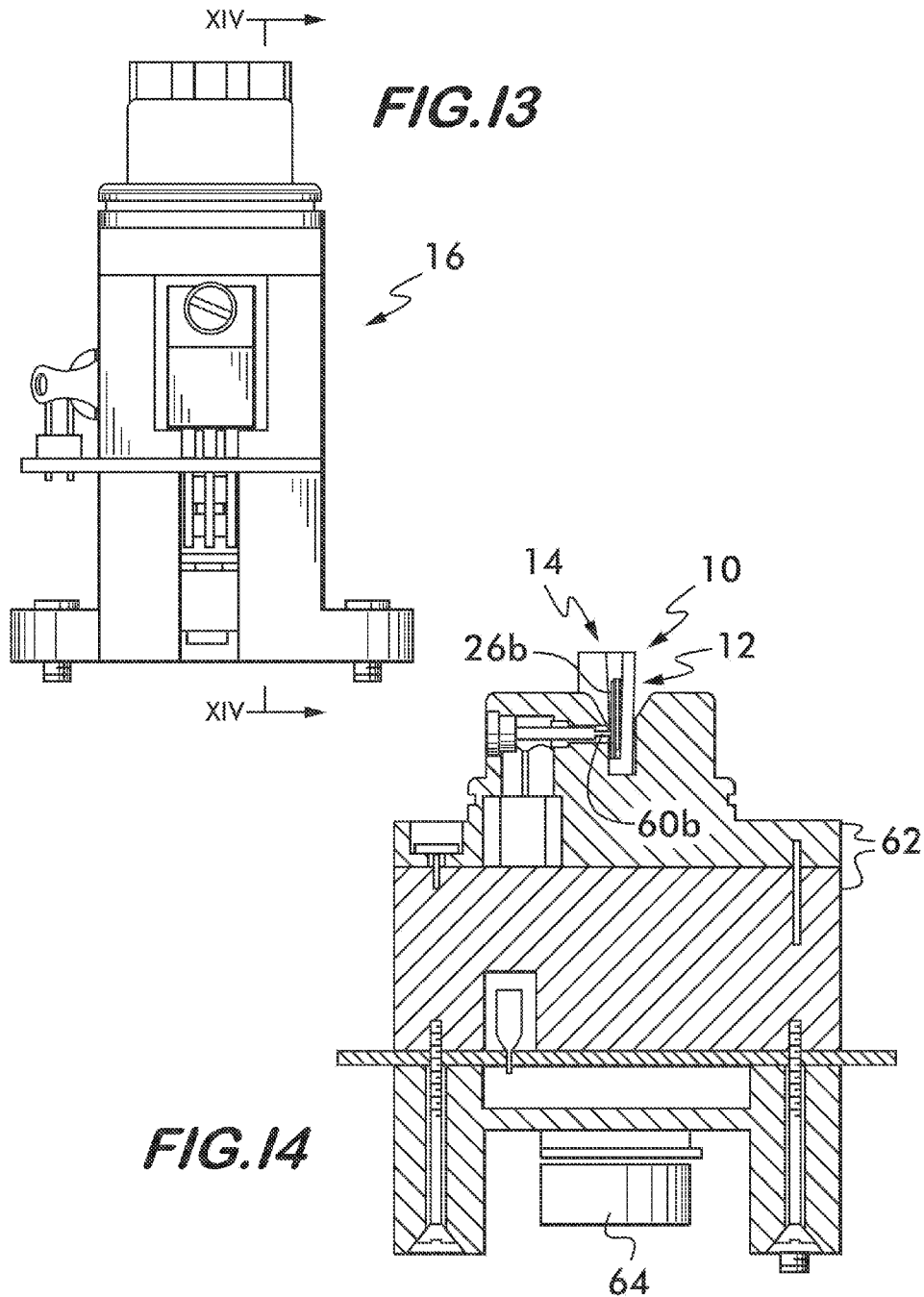

PLATELET AGGREGATION TEST AND DEVICE

FIELD OF THE INVENTION

This invention relates to devices for measuring platelet aggregation.

BACKGROUND OF THE INVENTION

Platelets are a component of blood that can aggregate when necessary for wound healing, for example. However testing platelet aggregation can reveal signs of a bleeding disorder or risk of thrombosis, or if a patient is not responding to antiplatelet therapy. Platelet aggregation tests can help diagnose problems with platelet function and determine whether the problem is due to one's genes, another disorder, or a side effect of medicine.

Platelets are known to aggregate under a variety of conditions and in the presence of a number of different reagents. "Platelet aggregation" is a term used to denote the adherence of one platelet to another. When they aggregate, platelets change from a discoid shape to a more spherical form, extend long processes known as pseudopodia and become sticky. As a result, the platelets stick to one another and to the damaged tissue, thus plugging gaps or holes in the blood vessel wall. Although the primary response of platelets is to aggregate, a secondary release reaction may also occur, during which platelets release materials which accelerate the clotting process.

Platelets' ability or inability to respond to particular aggregating reagents is the basis for differentiating platelet dysfunction from normal, for example.

Aggregation can be induced in a sample by adding aggregating agents to platelet-rich plasma or whole blood. Platelet aggregation depends on the presence of calcium, fibrinogen and one or more plasmatic factors, and an aggregating agent. Platelet aggregation will vary with different aggregating agents and with their concentration.

One method of testing platelet aggregation is optical aggregometry. For example, in 1962, Born described the aggregation of platelets by ADP and modified a colorimeter to monitor continuously this aggregation in platelet rich plasma. These modifications included incubation at 37° C., stirring and recording the change in light transmission over time on a pen recorder. This method is commonly referred to as Light Transmission Aggregometry (LTA).

With LTA, platelets are in a suspension of plasma isolated from an anticoagulated blood sample by a relatively low centrifugal force centrifugation. This material is known as platelet-rich plasma (PRP). Platelet-poor plasma (PPP) is prepared by centrifuging the blood sample at a relatively high force.

The sample chamber or chambers in multiple channel instruments are heated to 37° C. Provision is made for stirring of the sample because platelet to platelet contact is necessary to the determination of in vitro platelet aggregation. A beam of light shines through the sample cuvette. Photodiodes detect the light able to pass through the sample. A sample cuvette containing PRP is measured and a sample cuvette containing PPP is measured. PRP is arbitrarily considered to be 0% light transmission or 0% aggregation; PPP is considered to be 100% light transmission or 100% aggregation. The difference in light transmission outputs from the photodiodes is transferred to recording devices.

When an agonist or aggregating agent is added to the cuvette containing PRP and the platelets respond, changes in light transmission occur and are recorded over time by the recording device.

When the platelets undergo shape change in response to an agonist, their larger size allows less light to pass through the PRP: this is recorded as less light transmission through the sample relative to the PPP. If the dose of aggregating agent is strong enough to cause the platelets to adhere to each other and form aggregates, more light is able to pass through the PRP sample. The change in light transmission recorded, over time, shows a trend towards the platelet poor plasma, or 100% light transmission.

As is well known, in-vitro aggregation recordings are characterized by their appearances:
shape change
a first wave of aggregation (primary aggregation) that may reverse and return towards the PRP baseline
Irreversible second wave aggregation that occurs when the platelets' secreted granule contents become the stimulus and cause additional aggregation.

Aggregation curves are also characterized by:
the maximum amount of change in light transmission caused by the agonist (percent aggregation)
the slope- or rate-of the aggregation, in % change of aggregation per minute.

Multiple aggregating agents and dosages are usually used to stimulate the platelets. Different aggregating agents stimulate different pathways of activation in the platelets: either binding sites or metabolic pathways. Different concentrations of agonists are used to elicit a family of curves (dose response curves).

The pattern of responses to these test panels is compared to established normal response patterns and established abnormal response patterns. This information is considered to relate to the platelet function component of homeostasis.

In 1980, Cardinal and Flower described an impedance method for measuring aggregation in whole blood (U.S. Pat. No. 4,319,194). In their method, a very small electric current is passed between two electrodes. During initial contact with the blood the electrodes become coated with a monolayer of platelets. When an agonist is added, platelets aggregate on the monolayer increasing the impedance. This increase in impedance is recorded on a pen recorder.

In the impedance method, platelets are tested in anti-coagulated blood, without the need to isolate them from other components of blood. Because there is no need to centrifuge the specimen to produce an optically transparent suspension of cells, the entire platelet population is tested. The process of testing consumes less technical time; and labile factors in the blood itself that may influence platelet function are preserved.

A typical impedance aggregometer consist of a sample chamber or chambers (in multiple channel instruments,) heated to 37° C. The device typically includes apparatus to stir the samples, commonly utilizing non-magnetic disposable stir bars. Cuvettes containing the test sample and a stir bar are placed in the chamber(s).

The impedance (or electrical resistance) method of aggregation is non-optical. An electrode probe assembly is inserted into a cuvette containing a test sample. The electrode probe assembly consists basically of two precious metal wires that are immersed in the sample. An AC voltage in the millivolt range is applied to the probe circuit. The instrument measures the electrical resistance or impedance between the two immersed wires.

During a brief period of equilibration, a monolayer of platelets forms on the exposed portions of the wires, resulting in a stable impedance value. This stable baseline of impedance is assigned a value of zero ohms of resistance. An agonist is added to the cuvette and the stimulated platelets aggregate to the platelet monolayer on the immersed wires. This accumulation of platelets adds electrical resistance to the circuit. The changes in resistance are measured and quantified in ohms (the measurement of electrical resistance). The impedance measurement of the aggregated sample is generally run continuously for four to six minutes after the addition of an agonist.

Results of impedance aggregation tests are quantified by:
Ohms of aggregation at a given time in the test
Slope, or rate of the reaction, in ohms change per minute
Maximum extent of aggregation, in ohms.

The increase in impedance is directly proportional to the mass of the platelet aggregate. Impedance aggregation in blood is more sensitive to the aggregating effects of ristocetin so it may be more sensitive to von Willebrand disease than the bleeding time or vWF (ristocetin co-factor) assay. Impedance aggregation in blood is not dependent on the optical characteristics of the sample, so tests can be performed on lipemic and thrombocytopenic samples. As centrifugation is not required, impedance aggregation is especially useful in conditions where megathrombocyte count is increased.

The impedance method allows the study of platelets in the more physiologically representative whole blood environment. Sample preparation is greatly simplified, and preserves labile modulators such as prostacyclin and thromboxane A2, resulting in a testing environment proven to be more sensitive to the effects of many anti-platelet drugs (e.g., aspirin, dipyridamole, abciximab, clopidogrel, ticagrelor, ticlopidine, prasugrel, etc. . . . ).

In 1984, Freilich developed a low cost disposable electrode for measuring impedance aggregation by substituting for the wire electrodes conductive ink printed on a plastic nonreactive base (U.S. Pat. No. 4,591,793). This device is less expensive than the Cardinal device and is disposable after each test; however, there are disadvantages to the Freilich device. The platelets have difficulty adhering to the exposed conductive surface of the Freilich device, probably due to the surface being thin. Sometimes the aggregated platelets break off the surface, causing a sudden change in impedance. Although the Freilich device is inexpensive to manufacture, the measurements returned by the device can be inconsistent and not reproducible.

In 1997 Freilich et al. developed an improved low cost disposable electrode that overcame the reproducibility problems of their prior device (see, U.S. Pat. No. 6,004,818). The inventors discovered that the most reproducible configuration has the electrodes side-by-side with respect to the flow pattern. This configuration allows the platelets to stick to the face and the area between the electrodes, facilitating the formation of a bridge of platelets between the electrodes, which results in a stronger bond of platelets to the electrodes.

This device consists of two metal plates with a connection tab at one end and tip at the other end. The two plates are separated by an electrical insulator comprised any non-conducting material, such as mylar, plastic or teflon, which will separate the electrodes by the proper amount. Except for the tips, the plates are isolated from the sample by a non-conductive coating comprised of any insulating material, such as plastic or epoxy, which is non-reactive with the blood sample. The electrode tips are side by side with respect to the flow pattern. The tips are non-circular in cross-section, preferably rectangular, and most preferably square. The advantages of square tips are that at least one planar face of one electrode tip is adjacent and parallel to at least one planar face of the opposing electrode tip. Also, the square electrode tips are easier to produce than round electrode tips because a stamping process can be used to make the electrode out of flat metal to form an electrode plate.

The position fixing means are either a pair of molded plastic, semi-circular fins extending outwardly from the molded plastic coating the electrodes or molded plastic parts with slots for the placement of the electrodes. It is of considerable importance to keep the electrode tips in the proper placement in the cuvette so it is necessary to have these elaborate means to hold the electrode assembly in place.

There are several disadvantages to this device, which prevented it from ever going to market. First although it is less expensive than the Cardinal and Flower device, it is still too expensive to be disposable in today's cost conscious laboratory. Additionally, this device is difficult to manufacture which would result in a high rejection rate. Therefore this device has never been produced nor sold.

However, a variation of this device was produced and sold. This device used Square electrode pins held in the optimal position in the sample. The main difference is instead of plates the pins were attached to a kapton strip that had electrical circuit lines on it These circuit lines electrically connected the pins to tabs at the top of the a kapton strip. These tabs are used as contacts for connecting to the electrical circuit of the instrument.

This design works well in a 1 mL sample, however, when it was adapted it to a smaller sample, there was a spontaneous reaction of the platelets most likely due to a sheer force in the smaller sample cuvette. This spontaneous reaction makes this device unusable in a small sample cuvette. The small sample size is more beneficial because less patient blood is needed to run the assay.

Because the prior design failed when it was adapted to fit a smaller sample, there is a need for a workable electrode for smaller blood samples. This electrode needs to be easy to use and low cost and have the ability to test platelet function in whole blood in a small sample size.

The prior design was used in a 1 mL sample size, in a large cuvette (0.44"×1.83"). With the new device, the sample size will be from 250 μL to 300 μL. This smaller sample size requires a smaller sample cuvette with provision to stir the sample at 1000 RPM, the traditional stirring speed for platelet aggregation.

SUMMARY OF THE INVENTION

This invention is an assembly for measuring platelet aggregation comprising an electrode subassembly and a cuvette subassembly.

The electrode subassembly comprises:
i. an electrically non-conductive substrate with two wings at its top extending horizontally away from each other in opposite directions with a downwardly extending member;
ii. a pair of electrode contact pads separated from each other and mounted on the wings of the substrate, each contact pad having an electrically conductive lead extending downwardly on the downwardly extending member of the substrate, each lead having electrically connected to it a conductive wire extending below and downwardly away from the downwardly extending member, each of the two wires having a horizontal cross-section that is rounded with a cross-sectional dimension from about 0.17 to about 0.38 mm, where the portions of the two wires that extend downwardly away are substantially parallel, are spaced from one another about 0.18 to about 0.42 mm apart and are from about 1.9 to about 4.5 mm long;

And the cuvette subassembly comprises:

i. a lower reservoir to receive a sample containing platelets, the lower reservoir having a substantially flat, closed bottom and having a substantially cylindrical wall, the lower reservoir having an internal volume of from about 225 to about 375 μL, the reservoir adapted to receive a sample containing platelets;

ii. extending upwardly from the lower reservoir, an upper body comprising:

a. a pair of arms and a back member with a slot formed between each arm and the back member, each slot adapted to receive a wing from the electrode subassembly;

b. the dimensions of the cuvette subassembly being such that when the wings of the electrode subassembly are positioned in the slots, the two wires are positioned in the reservoir and above the bottom of the reservoir and adapted to be submerged in a sample placed in the reservoir;

c. a channel from an upper part of the cuvette subassembly to approximately the upper part of the reservoir, adapted to allow reagent to be placed into the sample without substantially interfering mechanically with the electrode;

The assembly also can include a stir bar adapted to be placed in the bottom of the cuvette well and free to rotate under the influence of an outside source to create a flow of sample in the well and between the two wires of the electrode subassembly when the electrode subassembly is mounted in the cuvette subassembly, the distances between bottom ends of the two wires and the bottom of the lower reservoir being such that the stir bar can fit in that distance and still create such flow.

Other aspects of the invention are described below.

BRIEF DESCRIPTION OF THE DRAWINGS

FIG. 1 is a perspective view of the electrode subassembly of this invention.

FIG. 2 is a front view of the electrode subassembly of this invention.

FIG. 3 is a side view of the electrode subassembly of this invention, viewed from the right side of FIG. 2.

FIG. 4 is a perspective view of the cuvette subassembly of this invention.

FIG. 5 is a top view of the cuvette subassembly of this invention.

FIG. 6 is a bottom view of the cuvette subassembly of this invention.

FIG. 7 is a cross-sectional view of the cuvette subassembly of this invention taken along the plane of line VII-VII of FIG. 6.

FIG. 8 is a rear view of the cuvette subassembly of this invention with the electrode subassembly of this invention inserted into it.

FIG. 8A is a rear view, partially in shadow of the electrode subassembly inserted into the cuvette subassembly of this invention with a stir bar in place.

FIG. 10 is a perspective view of a heater block/stirrer assembly used with the cuvette and electrode subassemblies of this invention, with those subassemblies placed into the heater/stirrer assembly.

FIG. 11 is a first end view of a heater block/stirrer assembly used with the cuvette and electrode subassemblies of this invention, with those subassemblies placed into the heater/stirrer assembly.

FIG. 12 is a cross-sectional first end view of a heater block/stirrer assembly used with the cuvette and electrode subassemblies of this invention, with those subassemblies placed into the heater/stirrer assembly, taken along the plane of line XII-XII of FIG. 11.

FIG. 13 is a second end view of a heater block/stirrer assembly used with the cuvette and electrode subassemblies of this invention, with those subassemblies placed into the heater/stirrer assembly. This second end view is the opposite end from the first end view.

FIG. 14 is a cross-sectional second end view of a heater block/stirrer assembly used with the cuvette and electrode subassemblies of this invention, with those subassemblies placed into the heater/stirrer assembly, taken along the plane of line XIV-XIV of FIG. 13.

DETAILED DESCRIPTION OF THE PREFERRED EMBODIMENT

Figure 9:
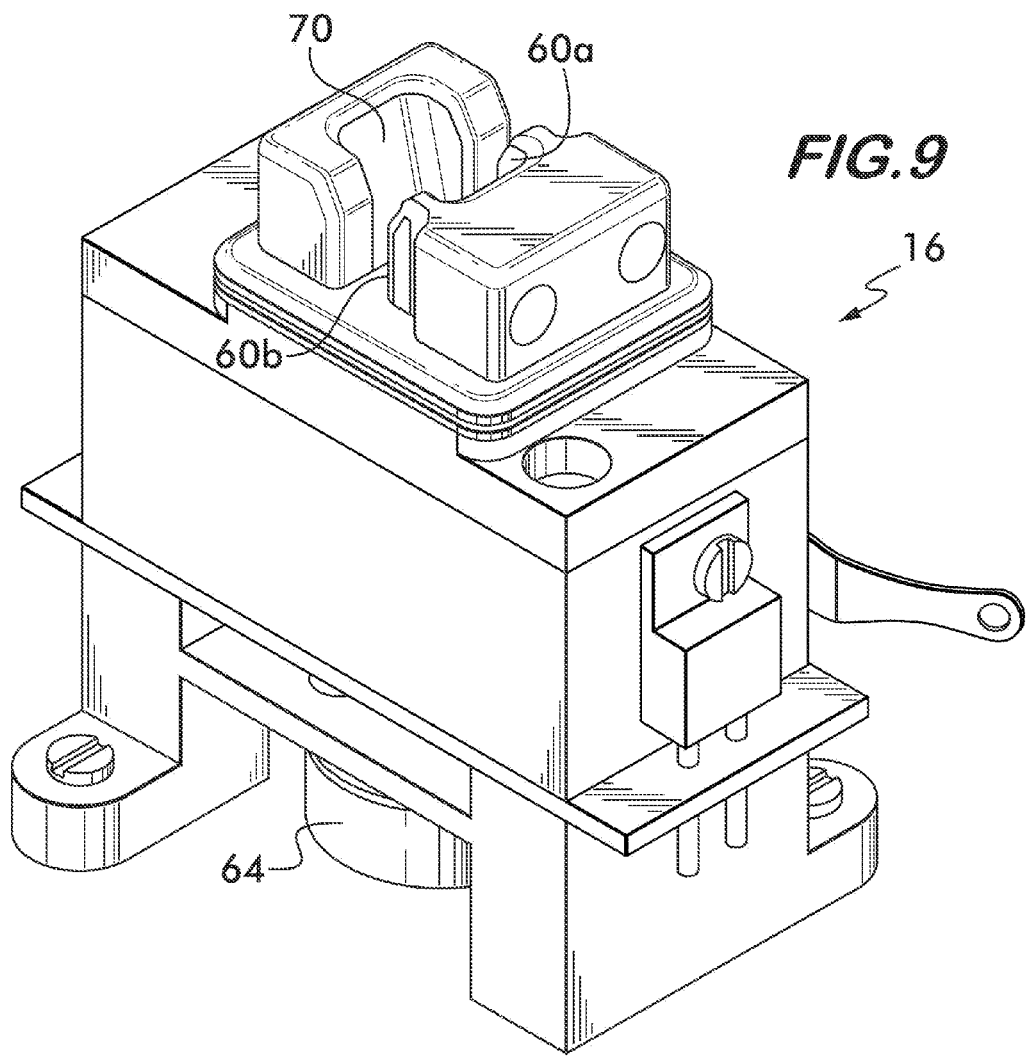
FIG. 9 is a perspective view of a heater block/stirrer assembly used with the cuvette and electrode subassemblies of this invention.

This invention includes a disposable assembly (or kit) 10 (see FIG. 8, for example) for measuring platelet aggregation in a sample. The sample can be whole blood or a blood component containing platelets. For reference purposes, we use the terms "front," "back," "upper," and "lower" to orient the reader and assist in his/her understanding of the invention. We could have just as easily used terms such as "first" and "second" or "left" and "right" or "distal" and "proximal." Our choice of terms of orientation is not meant to limit the scope of this invention, if one wants, for example, to create a mirror image of this invention or rotate its elements in space.

The disposable assembly 10 for measuring platelet aggregation includes an electrode subassembly 12 (see FIGS. 1-3, 8, 10, 12 and 14) and a cuvette subassembly 14 (see FIGS. 4-8, 10, 12 and 14). The disposable assembly is used with a heater/stirrer assembly 16 (see FIGS. 9-14). Disposable assembly also utilizes a stir bar 18 (FIGS. 8A and 12) that will be discussed further below.

Electrode subassembly comprises an electrically non-conductive substrate 20 (FIGS. 1-3) with two wings (22a and 22b)(see also FIG. 8) at its top extending horizontally away from each other in opposite directions with a downwardly extending member 24.

On substrate 20 are pair of conductive electrode contact pads 26a, 26b (FIGS. 1-3, 8 and 12) separated from each other and mounted on the wings of the substrate, each contact pad having an electrically conductive lead 28a, 28b mounted on and extending downwardly on the downwardly extending member 24 of the substrate. By "mounted on" we mean any kind of mounting but preferably by electrodeposition. The leads 28a and 28b are preferably coated with a non-conductive material (e.g., polymeric) to avoid exposure of those leads to the test sample when the electrode subassembly 12 is mounted in the cuvette subassembly with a sample in the cuvette reservoir.

Each lead (or tracing) 28a, 28b has electrically connected to it a conductive wire 30a, 30b extending below and downwardly away from the downwardly extending member 24. Each of the two wires having a horizontal cross-section that is rounded with a cross-sectional dimension from about 0.17 to about 0.38 mm. By "rounded" we mean oval, circular and the like as opposed to square or rectangular with sharp edges. The wires are preferably made from palladium (or its alloys), but other metals such as platinum, rhodium, gold, iridium, osmium, rhenium and ruthenium or alloys of the same can also be used.

As shown in FIGS. 1, 2 and 8A, the portions of the two wires 30a and 30b that extend downwardly away are substantially parallel, are spaced from one another about 0.18 to about 0.42 mm apart and are from about 1.9 to about 4.5 mm long (as measured from points d and e on FIGS. 2, 3 and 8a, those points identifying the portions of wires 30a, 30b that are not overlaying substrate 20). As shown in FIGS. 1-3 and 8A, member 24 has a lower, narrow protuberance 32 on which the upper ends of wires 30a and 30b are mounted. The purpose of narrowing the lower part of member 24 to a protuberance 32 is ultimately to allow the sample, under influence of stirring as described below, to flow around the fluid reservoir of cuvette 14 as evenly as possible, and around and between the wires during stirring.

To lend some optional structural support to substrate 20 and particularly wings 22a, 22b, one can add a rigid or semi-rigid polymeric reinforcing member 34 across the wings (FIGS. 1 and 3). The additional thickness and strength that member 34 provides affords a better fit—preferably an interference fit—into tapered slots 38a, 38b (see e.g. FIGS. 4, 5 and 7) in cuvette subassembly 14 as described below.

Finally, electrode subassembly 12 preferably includes an electrically non-conductive spacer element 36 (FIGS. 1-3, and 8A) fixed to the lower ends of wires 30a and 30b to assist in holding them in a fixed parallel position to each other. Both the substrate 20 and the spacer element 36 are preferably made from polyimide film, preferably Kapton brand.

The cuvette subassembly 14 of this invention (e.g., FIGS. 4, 7, 8 and 8A) includes a lower reservoir 40 to receive a sample containing platelets. The lower reservoir has a substantially flat, closed bottom 42 and a substantially cylindrical wall 44. By "substantially cylindrical," we do not mean to exclude some tapering that is illustrated in the drawings. Lower reservoir 40 has an internal volume of from about 225 to about 375 μL, and the reservoir is adapted to receive a sample containing platelets.

Extending upwardly from lower reservoir 40 is an upper body 46 (FIGS. 4 and 7) that includes a pair of arms 48a, 48b. Upper body 46 also has a back member 50 that creates a slot 38a, 38b (preferably tapered) between each arm 48a, 48b and back member 50, each slot is adapted to receive a wing 22 from the electrode subassembly (see FIGS. 4, 5, 7, and 12). As mentioned above, slots 38a, 38b are tapered, being wider at the top than the bottom 52 (FIGS. 7 and 12). As mentioned above, the wings 22a, 22b with reinforcing member 34 behind them create a thickness which in this case is adapted to fit snugly into the bottom 52 of each of the slots 38a, 38b. This preferred fitment holds the electrode subassembly into the cuvette subassembly so that the two hold relatively fixed positions relative to one another when assembled and in use.

The dimensions of cuvette subassembly 14 are such that when the wings of the electrode subassembly 12 are positioned in slots 38a, 38b, the two wires 30a and 30b are positioned in reservoir 40 and above the inside bottom of reservoir 40 and adapted to be submerged completely in a sample placed in reservoir 40. In addition, the dimensions of the two subassemblies 12 and 14 are such that there is sufficient space between spacer element 36 and the inside bottom of reservoir to allow a magnetically drivable stir bar 18 to fit easily and without interference on the inside bottom of the reservoir (see, e.g., FIGS. 8A and 12).

In addition, as shown in FIG. 8A, on electrode subassembly 12, the protuberance 32, wires 30a and 30b are not centered on downward member 24. Instead these elements are offset relative to the center of reservoir 40 such that when stirrer bar 18 is spun, these elements are not in the center of the circular flow of sample where sample fluid movement is slower, but rather in an offset location where fluid flow is faster.

Cuvette subassembly 14 (and specifically upper body 46) further includes a downwardly sloping channel 54 (FIGS. 4, 5, 7 and 12) sloping downwardly from an upper part of the cuvette subassembly to the approximately the upper part of reservoir 40. Channel 54 thus allows reagent(s) to be placed into a sample in reservoir 40 (usually by pipette) without the reagent placement substantially interfering mechanically with electrode 12.

Cuvette subassembly 14 also includes a pair of rearwardly projecting flanges 56a, 56b that extend rearward from arms 48a, 48b, forming a pair of sidewalls on the cuvette that reduce the chance of hand contact with the electrode subassembly 12 inside the cuvette subassembly 14. In addition, the lower ends of flanges 56a and 56b rest on the heater/stirrer assembly 16 (see, e.g., FIG. 10) and assist in positioning the cuvette subassembly in the heater/stirrer assembly. The positioning and dimensions of flanges 56a and 56b each relative to back member 50 create a pair of openings 58a and 58b (see FIGS. 4-5 and 10 that allow a pair of electrically conductive contacts (or brushes) 60a, 60b (see FIGS. 9, 10 and 14) mounted on heater/stirrer assembly 16 to make electrical contact with pads 26a and 26b when assembly 10 is mounted in assembly 16 as shown in FIGS. 10 and 14.

Assembly 10 preferably operates with stir bar 18 (FIGS. 8A and 12) adapted to be placed in the bottom of the cuvette reservoir 40, and free to rotate under the influence of an outside source to create a flow of sample in the well and between the two wires 30a and 30b of the electrode subassembly when the electrode subassembly is mounted in the cuvette subassembly, the distances between bottom ends of the two wires and the bottom of the lower reservoir being such that the stir bar can fit in that distance and still create such flow.

The heater/stirrer assembly 16 (FIGS. 9-12) includes a heater block 62 that contains a well 63 (FIG. 12) that receives reservoir 40 when cuvette subassembly 14 is mounted in assembly 16. The heater block has a heating element (not illustrated) that can warm the block and the reservoir to an appropriate temperature (i.e. about 37° C.) for sample analysis.

Heater/stirrer assembly 16 (FIG. 12) also includes a stirrer motor 64 that is operably connected via a motor shaft 66 to turn a magnetic stirrer 68, which proximate enough to the bottom of reservoir 40 such that stirrer 68 can spin stir bar 18 in the bottom of reservoir 40 when stirrer 68 is spun by motor 64. Thus, the sample in reservoir 40 can be mixed and circulated between wires 30a and 30b.

The upper portion of heater block 62 has a recess 70 (FIGS. 9 and 12) that generally conforms to the shape of cuvette subassembly 14 to hold the cuvette subassembly 14 steady when in use and to allow good thermal contact with the cuvette subassembly to allow the sample to be heated.

This invention allows for the monitoring of platelet aggregation in a small sample size, using a low-cost disposable electrode assembly. This electrode assembly consists of an electrode, a plastic cuvette and a stir bar, which fits into a sample chamber. The sample chamber is heated at 37° C. and the stir bar is typically spun at 1000 RPM but can be spun from 500 to 1200 RPM. The electrode has two fine palladium alloy wires evenly spaced with both ends secured to Kapton. A small voltage difference is applied through contacts 60, and ultimately across wires 30a and 30b to measure the impedance of the sample. These wires are set apart about 0.18 to about 0.42 mm apart, which is close enough to allow a platelet aggregation plug to bridge the wires and produce a stable result. The new electrode configuration allows the wires to be completely submerged in a smaller sample volume. The position of the wires is important to accurate test results. The electrode wires should be completely submerged within the sample (i.e. are completely covered by the sample). When completely submerged the location of the wires should be where there is sufficient stiffing with an even flow pattern, and where the wire electrodes do not interfere with the stir bar.

The cuvette subassembly can be a made from plastic so it can produced at a low cost using injection molding. The cuvette was designed with the following features so that it fits this use:

Sample chamber is small enough so that electrode wires are completely submerged in a smaller sample volume.

Two slots 38a and 38b for holding the electrode subassembly securely in the position that thereby fixes the electrode wires in the optimum position in the sample.

A flat-bottom reservoir 40 so that the stir bar 18 spins without interference, which stirs the sample evenly and consistently.

Reinforcement member 34 at the top of the electrode subassembly, located behind the contact pads 26a, 26b of the electrode, which adds support to the substrate 20 when in contact with contacts 60.

A channel 54 from the top of the cuvette subassembly to the approximately mid-point, so that the pipette tip, used for dispensing the reagent/agonist, can be inserted into the sample without bumping against the electrode.

The cuvette is inserted into a sample chamber heated to 37° C. The sample chamber consist of two parts, a socket, which has two spring loaded contacts 60 that make electrical contact with the contact pads 26a, 26b, and a heater block, which contains the heating element and temperature sensors. Mounted below the heater block is a motor 64 and magnet assembly 68 which when power is applied, spins at 1000 RPM. The magnet mounted on the motor provides a magnetic force that spins the stir bar in the cuvette. There are cables and connectors mounted to the heater block assembly that connects components embedded in the heater block assembly to a printed circuit board ("PCB"; not shown).

On the PCB are conventional circuits which measure changes in resistance that occur in the sample after the addition of an agonist. As is well known, the results of impedance aggregation tests are quantified by:

Ohms of aggregation at a given time in the test
Slope, or rate of the reaction, in ohms change per minute
Maximum extent of aggregation, in ohms.

The results can be recorded on a strip chart recorder or to a computer using available software.

We claim:

1. An assembly for measuring platelet aggregation, comprising:
   a. an electrode subassembly comprising:
      i. an electrically non-conductive substrate with two wings at the substrate's top extending horizontally away from each other in opposite directions with a downwardly extending member;
      ii. a pair of electrode contact pads separated from each other and mounted on the wings of the substrate, each contact pad having an electrically conductive lead extending downwardly on the downwardly extending member of the substrate, a conductive wire electrically connected to each lead, the conductive wire extending below and downwardly away from the downwardly extending member, each of the two wires having a horizontal cross-section that is rounded with a cross-sectional dimension from about 0.17 to about 0.38 mm, where the portions of the two wires that extend downwardly away are substantially parallel, are spaced from one another about 0.18 to about 0.42 mm apart and are from about 1.9 to about 4.5 mm long;
   b. a cuvette subassembly comprising:
      i. a lower reservoir to receive a sample containing platelets, the lower reservoir having a substantially flat, closed bottom and having a substantially cylindrical wall, the lower reservoir having an internal volume of from about 225 to about 375 μL, the reservoir adapted to receive a sample containing platelets;
      ii. extending upwardly from the lower reservoir, an upper body comprising:
         a. a pair of arms and a back member with a slot formed between each arm and the back member, each slot adapted to receive a wing from the electrode subassembly;
         b. the dimensions of the cuvette subassembly being such that when the wings of the electrode subassembly are positioned in the slots, the two wires are positioned in the reservoir and above the bottom of the reservoir and adapted to be submerged in a sample placed in the reservoir;
         c. a channel from an upper part of the cuvette subassembly to the approximately the upper part of the reservoir, adapted to allow reagent to be placed into the sample, without substantially interfering mechanically with the electrode;
   c. a stir bar adapted to be placed in the bottom of the cuvette well and free to rotate under the influence of an outside source to create a flow of sample in the well and between the two wires of the electrode subassembly when the electrode subassembly is mounted in the cuvette subassembly, the distances between bottom ends of the two wires and the bottom of the lower reservoir being such that the stir bar can fit in that distance and still create such flow.

2. The assembly of claim 1 wherein the cuvette subassembly arms each contains a flange, wherein an opening is formed between each flange and the back member where each opening allows electrical contact to be established with one of the contact pads from outside the assembly.

3. The assembly of claim 2 in combination with a heater block assembly adapted to receive the cuvette subassembly, wherein the contact pads and openings are arranged vertically when the assembly is mounted in the heater block assembly.

4. The assembly of claim 1 wherein when the wires are positioned on the substrate such that when the electrode subassembly is mounted in the cuvette subassembly, the wires are offset relative to the center of the reservoir.

5. The assembly of claim 1 wherein the wings of the electrode subassembly include a reinforcing member that overlay the wings, and the slots on the cuvette subassembly are tapered and dimensioned to receive the wings and reinforcing member with an interference fit to hold the electrode subassembly in a substantially fixed position in the cuvette subassembly when in use.

* * * * *